US009115395B2

(12) United States Patent
Wietzorrek

(10) Patent No.: US 9,115,395 B2
(45) Date of Patent: Aug. 25, 2015

(54) APPARATUS FOR PHOTOMETRIC MEASUREMENT OF BIOLOGICAL LIQUIDS

(71) Applicant: Roche Molecular Systems, Inc., Pleasanton, CA (US)

(72) Inventor: Joachim Wietzorrek, Zug (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 14/471,346

(22) Filed: Aug. 28, 2014

(65) Prior Publication Data
US 2015/0064699 A1 Mar. 5, 2015

(30) Foreign Application Priority Data

Sep. 2, 2013 (EP) .................................... 13182572

(51) Int. Cl.
| G01N 15/06 | (2006.01) |
| G01N 33/00 | (2006.01) |
| G01N 33/48 | (2006.01) |
| C12Q 1/68 | (2006.01) |
| G01N 21/25 | (2006.01) |
| G01N 21/64 | (2006.01) |
| G02B 3/00 | (2006.01) |

(52) U.S. Cl.
CPC .............. *C12Q 1/686* (2013.01); *G01N 21/253* (2013.01); *G01N 21/6452* (2013.01); *G01N 21/6486* (2013.01); *G02B 3/00* (2013.01); *G01N 2201/06146* (2013.01); *G01N 2201/0806* (2013.01)

(58) Field of Classification Search
USPC ........... 422/50, 400, 68.1, 82.05; 436/43, 164
See application file for complete search history.

(56) References Cited

U.S. PATENT DOCUMENTS

2008/0056950 A1   3/2008   Weisbuch et al.

FOREIGN PATENT DOCUMENTS

| EP | 0909947 A2 | 4/1999 |
| EP | 1681555 B1 | 3/2007 |
| EP | 1078245 B1 | 8/2008 |
| EP | 1959715 A1 | 8/2008 |
| EP | 2148187 A1 | 1/2010 |
| EP | 2693252 A1 | 2/2014 |

*Primary Examiner* — Brian J Sines
(74) *Attorney, Agent, or Firm* — M. Reza Savari

(57) ABSTRACT

An apparatus for photometric measurement of biological liquids and a method of simultaneously measuring the presence or quantity of an analyte in a sample region are disclosed. The apparatus includes a plurality of spaced apart sample regions; a light source adapted to emit light including at least one frequency; a lens system including a light coupling system, wherein the light coupling system is disposed between the light source and the plurality of sample regions. A method is also disclosed including illuminating the sample region with a light beam emitted from a light source, wherein said light beam passes a light coupling system, the light coupling system including a telecentric element and a plurality of light mixing rods, wherein the light coupling system is disposed between the light source and the sample region such that the light beam is directed into the sample region.

12 Claims, 10 Drawing Sheets

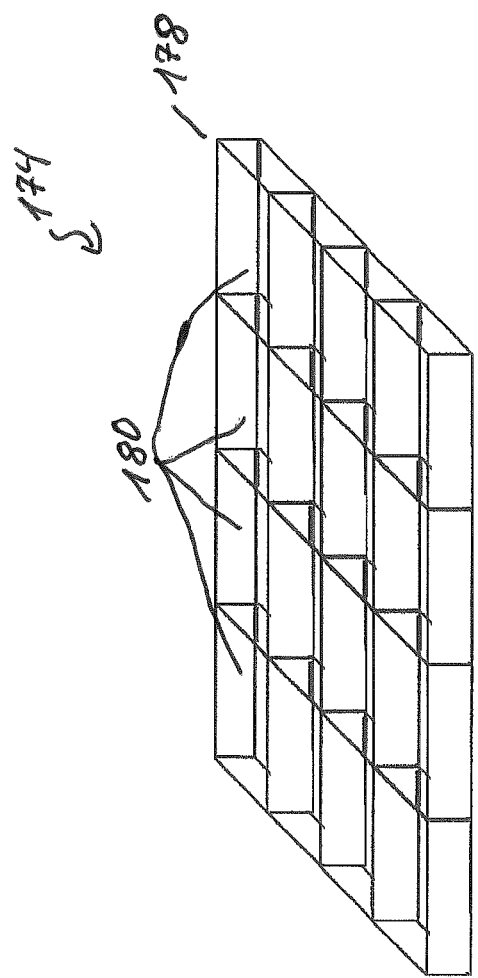

APPARATUS FOR PHOTOMETRIC MEASUREMENT OF BIOLOGICAL LIQUIDS

CROSS-REFERENCES TO RELATED APPLICATIONS

The present application claims the benefit of priority under 35 U.S.C. §119 of EP 13182572.1, filed Sep. 2, 2013, the content of which is incorporated by reference herein in its entirety.

FIELD OF THE INVENTION

The present disclosure relates to the field of photometric measurement of biological liquids, and in particular to an apparatus for photometric measurement of biological liquids comprising a light source, a lens system and a detector. The disclosure also provides an analytical device for measuring an analyte comprising such an apparatus, and an analytical system comprising such an analytical device. The disclosure further provides a method for simultaneously measuring the presence or quantity of an analyte in a sample region.

BACKGROUND OF THE INVENTION

Lens systems for amplification instruments are well known in the art. One example of such a lens system is shown in U.S. Pat. No. 7,906,767. The lens system comprises a field lens, a field lens array and a pupil lens array. Such lens systems may be used for photometric measurement of biological liquids. Respective apparatus comprise a light source, a detector and such a lens system, wherein said lens system comprises a field lens array.

The present disclosure provides an apparatus, system, and method for photometric measurement of biological liquids, displaying several advantages.

SUMMARY OF THE INVENTION

It is an objective of the present disclosure to provide an improved apparatus for photometric measurement of biological liquids comprising a light source, a lens system and a detector. It is a further objective of the present disclosure to provide an improved analytical device for measuring an analyte comprising such an apparatus. It is a further objective of the present disclosure to provide an improved analytical system comprising such an analytical device. It is a further objective of the present disclosure to provide an improved use of such an apparatus for photometric measurement of biological liquids. It is a further objective of the present disclosure to provide an improved method of simultaneously measuring the presence or quantity of an analyte in a sample region An improved method and a device for photometric measurement of biological liquids with the features of the independent claims is provided. Specific embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

An apparatus for photometric measurement of biological liquids is disclosed, comprising:
 a plurality of spaced apart sample regions;
 a light source adapted to emit light comprising at least one frequency;
 a lens system comprising a light coupling system, wherein the light coupling system is disposed between the light source and the plurality of sample regions, the light coupling system comprising at least one telecentric element and a plurality of light mixing rods, wherein each sample region is assigned at least one of the light mixing rods, wherein the telecentric element is disposed between the light source and the plurality of sample regions and the plurality of light mixing rods is disposed between the telecentric element and the plurality of sample regions;
 a detector disposed to receive light beams originating from the plurality of sample regions,
 wherein an optical detection system is further disposed between the plurality of sample regions and the detector, said optical detection system comprising the telecentric element and the plurality of light mixing rods such that the light originating from the plurality of sample regions passes the telecentric element and the plurality of light mixing rods of the optical detection system.

Said telecentric element may be independently selected from a field lens, a refractive field lens, a merged refractive field lens, a Fresnel field lens, a prism array, a Fresnel prism array, prisms. Said telecentric element and the plurality of mixing rods may be physically separate units. The telecentric element and the plurality of mixing rods may be in physical contact with each other.

The plurality of light mixing rods shall be tapered such that a narrower end of each light mixing rod faces the plurality of sample regions. Using a plurality of tapered light mixing rods offers several advantages as will be specified in more detail below.

A first advantage is a higher efficiency. Particularly, regarding the excitation, tapered light mixing rods have the advantage to collect all the excitation light from the light source such that it is homogeneously distributed in the field plane, and then to guide it into the individual or associated sample regions. Further, a waste of light on the rims between the plurality of sample regions is prevented. Therefore, the so-called fill factor of the illumination is augmented to 100% despite the physical distances between the plurality of sample regions as the tapered light mixing rods concentrate the light from the larger end onto the narrower end. In the excitation or illumination light path, the cross-section at the exit end of each light mixing rod is smaller than the cross-section at the entrance end in the field plane resulting in a higher numerical aperture of the illuminating light at the narrower end of the rod. This higher numerical aperture can be of further advantage for homogenously illuminating the sample in the sample regions. Regarding the emission, the emission light that is emitted by the sample regions enters the tapered light mixing rods through their narrower end and is being guided onto their broader end. The array of broader ends of the tapered light mixing rods builds another field plane. The light mixing rods do not add any optical power to the optical system. The light is simply guided internally and no imaging takes place through the rods, so this is like a shift of the object, where the object consists of the sample regions. Further, as the cross-section is enlarged through the tapered rod, the resulting numerical aperture in the field plane is smaller than the original numerical aperture from the sample regions. With other words, because the distribution of light onto a larger cross-section reduces the angles, the beams also diverge, and, therefore its numerical aperture. Therefore, having a smaller numerical aperture at the field plane is a significant advantage for capturing the maximum possible portion of light by the following optics as the coupling efficiency into the detection optics is increased by a smaller numerical aperture. More beams match the aperture of the detection optics than beams with a larger angle of divergence.

A second advantage is the reduction of crosstalk. Particularly, another advantage of using such tapered light mixing rods is the smaller number of optical surfaces that are present in the light path and have to be crossed by the light beams. Fewer surfaces means less loss of light as well as a reduction in reflections that occur every time a beam transits a surface. Such reflections always bear the risk of so called ghost signals and/or crosstalk, which both lead to wrong signals. This advantage is reached best by merging a field lens or an array of prisms directly onto that field plane that consists of all the larger end planes of each light mixing rod. This field lens or array of prisms is used to direct the signals from the outer wells towards the center of the aperture of the detection optics.

A third advantage is a reduced dependency on tolerances. Particularly, using such an array of tapered light mixing rods further reduces the dependency on tolerances as known from using arrays of pupils, vial lenses and field lenses such as described in U.S. Pat. No. 7,906,767. Vial lenses and field lens arrays provide large optical power to the system which makes the respective systems highly dependent on tolerances. Light mixing rods do not provide optical power at all. Therefore, they are very insensitive to tolerances. The rods can be simply aligned with the array of sample regions. This arrangement is much simpler than aligning multiple lens arrays. Also the distance in the light propagating direction between the plurality of sample regions and the field lens is unchangeably given by the dimension of the plurality of tapered light mixing rods. If said tolerances become too large in the case of lens arrays instead of rods, the detected signal lacks uniformity.

Theoretically, the plurality of tapered light mixing rods in combination with a field lens or a field lens array generate the same light path as the one described in U.S. Pat. No. 7,906, 767 but the optical efficiency is further improved and the possibility of crosstalk is reduced. Further, due to the absence of optical power between the plurality of sample regions and the field lens, larger tolerances can be accepted in the assembly with no negative effect. Each of the plurality of tapered light mixing rods is adapted to guide the light to the next optical plane and to transform it in a way to match it best onto the following optics.

The telecentric element and the plurality of light mixing rods may be at least partially made of glass or plastics. The telecentric element and the plurality of light mixing rods may be bonded, adhered welded or mechanically connected to one another. The telecentric element and the plurality of light mixing rods may be integrally formed. The telecentric element and the plurality of light mixing rods may be integrally molded. A cover against stray light may be disposed between the plurality of light mixing rods. The cover may be a grid shaped plate. The plurality of light mixing rods may comprise at least 2, preferably at least 96 light mixing rods and more preferably multiples of 96 light mixing rods. The plurality of light mixing rods may comprise a rectangular cross-section. The plurality of light mixing rods may comprise a proximal end arranged at the telecentric element and a distal end facing the plurality of sample regions. The distal ends of each of the plurality of light mixing rods may be arranged in a common plane. The plurality of light mixing rods may comprise sharp edges, wherein the sharp edges are located at the distal ends of the rods. The distal ends of each of the plurality of light mixing rods may be smooth, convex, concave, slanted or angled. The proximal ends of each of the plurality of light mixing rods may comprise a greater numerical aperture than the distal ends. The proximal ends of the plurality of light mixing rods may contact each other or may be spaced apart from each other. The telecentric element may be a first telecentric element and the plurality of light mixing rods may be a first plurality of light mixing rods, wherein the apparatus may further comprise a plurality of light sources, a second telecentric element and a second plurality of light sources directly connected to the second telecentric element, wherein the second telecentric element may be disposed adjacent the first telecentric element such that the second plurality of light mixing rods faces the plurality of light sources. The light emitted from the light source may be excitation light. The light originating from the sample regions may be emission light. Alternatively, the light originating from the sample regions may be remission light. This is the case if fluorescent markers are not used and the remission of a colorant, for example, is detected.

An analytical device for measuring an analyte is disclosed, comprising an apparatus according to any preceding claim. The analytical device may be a PCR instrument for real-time detection of nucleic acids during amplification.

An analytical system is disclosed, comprising such an analytical device.

The apparatus of may be used for photometric measurement of biological liquids.

A method of simultaneously measuring the presence or quantity of an analyte in a sample region is disclosed, comprising:

illuminating said sample region with a light beam emitted from a light source, wherein said light beam passes a light coupling system, said light coupling system comprising a telecentric element and a plurality of light mixing rods, wherein the light coupling system is disposed between the light source and the sample region such that the light beam is directed into the sample region; and detecting a light beam originating from the sample region following illumination of the sample region, wherein said light beam originating from said sample region is focused onto a detector by an optical detection system disposed between the sample region and the detector.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

FIG. 10 shows a perspective view of a cover against stray light adapted to be used with an apparatus for photometric measurement of biological liquids.

DETAILED DESCRIPTION OF THE INVENTION

Figure 1:
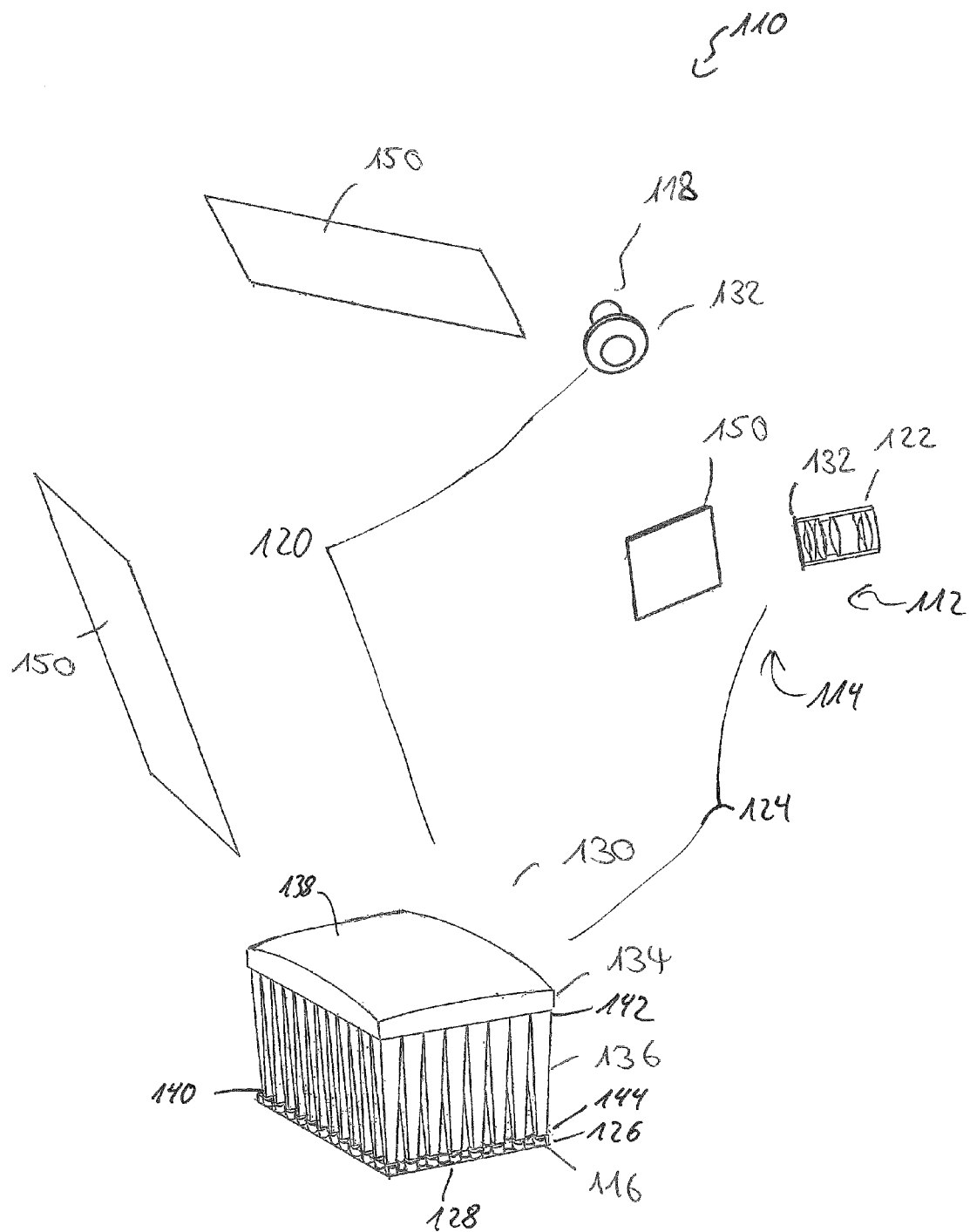
FIG. 1 shows a perspective view of an analytical system according to a first embodiment.

By way of illustration, specific exemplary embodiments in which the invention may be practiced now are described.

The term "light source" as used herein can be any kind of illuminator that can be used for excitation of luminescence generated in a sample to be analyzed. The light source can be a primary or a secondary light source, wherein a primary light source changes electrical, electromagnetic, chemical, thermal, kinetic or any other form of energy, including e.g. light-emitting diodes based on fluorophores, into light suitable for excitation of a marker molecule in a sample region. A secondary light source is a light source which transforms the shape, direction and homogeneity of a light beam into another light beam. It can be a white source or can only contain a single wavelength, multiple wavelengths or one or more wavelength bands or combinations thereof. Typical light sources are incandescent lamps, gas discharge lamps, or light emitting diodes (LEDs) including organic LEDs (OLEDs). The light source includes illuminants emitting light with a single frequency or with a plurality of different frequencies. Additionally, the light source may be an arrangement of more than one of said illuminants.

The term "detector" as used herein relates to a specific arrangement of a plurality of individual detection sites that are located in the image plane of the image of the field plane. Each individual detection site is a device capable of capturing light and converting the light intensity into a corresponding electrical signal. The image of the fluorescence light originating from each sample contained in a well or vial or sample region coincides with at least one detection site. For example, the detector may comprise a charge-coupled device (CCD) chip adapted to convert the optical signal transmitted by the light beams into a graphical illustration on a monitor such that the user may recognize the result of his or her measurement.

The terms "originating light beams" as used herein relate to light beams originating from the sample regions. These light beams may be luminescence generated by excitation of marker molecules in the samples comprised in the wells or sample regions, i.e. emission light, or remission light if fluorescent markers are not used.

A "lens system" as used herein comprises one or more lenses or lens arrays and optionally mirrors or other optical elements such as reflectors located in the beam path between the field plane and the arrangement of a plurality of individual detection sites with the purpose of generating a sharp image of the field plane across the conceptual or physical pupils onto the image plane that may or may not coincide with the surface of the arrangement of individual detection sites.

The term "telecentric element" as used herein relates to an optical element with an aperture stop that is projected to infinity by the optical elements between the aperture stop and the object. In other words, the chief rays of a telecentric optic are quasi-parallel, in the object space. The term chief rays is used for all rays passing through the center of the aperture stop. The object is the sample region illuminated by the light source. Said telecentric element is telecentric for the excitation path and for the detection path. Each object point in a plane perpendicular to the optical axis corresponds to an excitation chief ray as well as a detection chief ray. Since all excitation chief rays as well as all detection chief rays are quasi parallel, a good lateral homogeneity in the object plane is assured and the sites located in the center of the assembly are comparable to those located at the border of the assembly. Throughout the present disclosure, a telecentric element may be selected from the group consisting of a field lens, a refractive field lens, a merged refractive field lens, a Fresnel field lens, a field lens array, a prism array, a Fresnel prism array, and prisms.

The term "field lens array" as used herein relates to a two dimensional array of field lenses all placed in or close to a field plane in an optical system. The array comprises more than one field lens array element. The "field lens array elements" may be individual field lenses.

The term "prism array" as used herein relates to a two dimensional array of prisms all placed in or close to a field plane in an optical system. The array comprises more than one prism array element. The "prism array elements" may be individual prisms.

The term "Fresnel lens" as used herein relates to a type of compact lens. The design allows the construction of lenses of large aperture and short focal length without the mass and volume of material that would be required by a lens of conventional design. A Fresnel lens can be made much thinner than a comparable conventional lens, in some cases taking the form of a flat sheet. A Fresnel lens can capture more oblique light from a light source, thus allowing the light from a lighthouse equipped with one to be visible over greater distances.

The term "field plane" as used herein relates to a plane that is imaged sharply onto a detector. Thus, a field plane is always located where a sharp image of an object plane is formed. An optical system may comprise one or more sharp intermediate images of an object plane and, thus, one or more field planes. The field plane is, furthermore, the location in which each light emission pencil is focused into a point. Thus, each lens positioned in a field plane has no refractive force towards these light emission pencils. A field lens does, thus, not focus a light beam, it deflects the light beam. If the field lens is not located exactly in the field plane, but is located close to the field plane, it is still a field lens if its focusing power, which depends on the focal length of the lens and its distance from the field plane, is small compared to the diameter of the beam so that the main effect of the lens is deflection, not focusing.

The term "sharp edges" as used herein relates to a shape of the edges which is not rounded or rounded with a very small radius of curvature.

The sample regions may be accommodated by chambers comprised in a block. The sample regions may be plastic vessels. For example, the sample regions are plastic vessels constructed and arranged to permit an optimal heat transfer between the block and a liquid comprised within said vessels. This allows for optimal conditions during thermocycling and ensures specificity and efficiency of the nucleic acid amplification. The liquid comprises reactants which can be detected by illumination with light beams. Examples of reactants are fluorescent labels which correlate with the formation of a reaction product in the liquid. One example of a reaction is an amplification reaction, such as TMA, NASBA or PCR. Such amplification reactions are well known in the art. Alternatively, the sample regions are multi well plates, i.e. wells arranged in a microtiter plate.

A basic idea of the present disclosure is to use a telecentric element for optimizing illumination of a plurality of sample regions for photometric measurement such as excitation and detection of fluorescent markers. For this purpose, an optical detection system is disposed between the plurality of sample regions and the detector, said optical detection system comprising the telecentric element and a plurality of light mixing rods, such that the light originating from the plurality of sample regions passes the telecentric element and the plurality of light mixing rods of the optical detection system. Thus, the telecentric element is used for excitation light as well as emission light or remission light which is located within or close to a field plane. In order to prevent crosstalk between the sample regions, the plurality of light mixing rods is provided through which the light emitted from the light source as well as the light originating from the sample region passes. Accordingly, the present disclosure simplifies the array of field lenses if compared to lens arrangements of the prior art as the light mixing rods separate the propagation of the light and the telecentric element as well as the light mixing rods may be reduced to a single mass product and a single lens.

The tapered ends of the light mixing rods preferably face the sample regions such that the light emitted from the light source is individually and evenly distributed to the associated sample regions. The tapered ends comprise a greater numerical aperture than within the coupling field plane. The broader ends of the light mixing rods may contact one another in a single area or may be spatially separated to a low degree with an assembled construction, i.e. a construction where the light mixing rods and the telecentric element are assembled together. This plane is imaged to the detector in a sharp manner. Therefore, it is optimal to directly arrange a field lens, a field lens array or a prism array at the broader ends representing the emission area for the excitation. For example, the field lens or the field lens array may be integrally formed with the light mixing rods such as being molded. The necessity for a physical transition between the light mixing rods and the telecentric element is prevented independent from whether the telecentric element is a single field lens, a rectangular field lens, a Fresnel lens or an array of field lenses, such as small, rectangular or square field lenses or Fresnel lenses.

As this plane, in which emission light beams from each sample region enter or are incident, is imaged in a telecentric and sharp manner onto the detector, crosstalk may not occur. A prevention of unlikely crosstalk through air between the respective light mixing rods may be realized by a guard or protection or cover against stray light, for example a grid shaped plate, which is disposed between the light mixing rods. In principle, the more the light mixing rods are laterally spaced apart within the emission side plane the better is the prevention of crosstalk. This is preferably realized by sharp transitions between the respective light mixing rods during injection molding, cutting or subsequently by means of a sharp polishing edge.

Thus, the efficiency of the light transmission is optimized in the direction of the light emitted from the light source as well as in the emission of the light originating from the sample regions.

The end faces of the light mixing rods are preferably plane and together form a plane. Alternatively, the end faces may be formed convex, concave, inclined or angled such as a gable or pyramid in order to direct the light emitted from the light source to desired sites within a sample region or to couple light from predetermined sites in an optimized manner. For example, this arrangement may be realized with magnetic beads which are fixed to predetermined locations in a sample region by means of a magnetic field or with optical measurements of coagulation reactions, wherein the coagulating blood or plasma is adhered to the walls of the sample regions.

The same optical constructional member may also be used in exclusively one propagation direction for illumination, which usually corresponds to the direction of the light emitted from the light source in that the respective light mixing rods are disposed onto an array of LEDs or other light sources such as OLEDs, halogen lamps or laser sources. The upper part may be designed such that the emitted light is coupled into the optical system having the desired characteristics. Thus, optimized telecentric illumination may be achieved with a field lens which is disposed in a plane convex manner. Light from a plurality of LEDs may be homogenized across an area but a mixture of different wavelengths of respective LEDs may be achieved by predefined allowance of crosstalk by premature or deeper located merging of the light mixing rods.

Instead of a single telecentric field lens, a lens or an array of lenses may be attached which induce a new direction for the light. Particularly, the emitting plane may be angled by means of a prism element disposed therebetween. A plane convex lens may form the upper end for the respective great light field. Single areas of one or more light mixing rods having each a lens disposed above may be imaged in other directions or other distances, which may be desired with a system having a plurality of detectors. For example, a single channel from one light mixing rod having a higher or less high forming lens or a lens with a different curvature may be imaged onto a separate single detector, which is optically located closer or farther away than the detector of the measuring system or laterally offset, for example in order to function as optical reference channel. Alternatively, the transparent material may be coated or colored different at different locations in order to adapt respective filter characteristics.

Further, it is possible to have light mixing rods with different lengths at the same telecentric element for deep well sample regions and sample regions having different fill levels or to have the orientation of the light mixing rods not parallel. By means of angled light mixing rods, reference light sources may be directed to the same detector at the same time as the measurement of fluorescent emission. Alternatively, signals from dry probe arrays may be measured perpendicular with respect to a plurality of sample regions.

Further examples for possible embodiments concerning the telecentric element and the light mixing rods are in that the telecentric element and the light mixing rods are formed as an injection molded member made of plastics or glass having 96, 384, 1536 (2 to 1600) or the like legs shaped as obelisks. Alternatively, a cut or polished member made of plastics having legs shaped as obelisks may be used. Tapered rods made of plastics or glass may be attached to the telecentric array so as to form an array and hold together. The rods may be attached to the telecentric element by means of adhering, welding, mechanically coupling, for example by means of a grid net or clamping. A plane convex lens may be attached to the larger upper ends of the conical legs. The lens may be adhered, welded, disposed or formed from one piece, for example by molding or cutting.

Summarizing the findings of the present disclosure, the following specific embodiments are described:

Embodiment 1

An apparatus for photometric measurement of biological liquids comprising:
a plurality of spaced apart sample regions;

a light source adapted to emit light comprising at least one frequency;

a lens system comprising a light coupling system, wherein the light coupling system is disposed between the light source and the plurality of sample regions, the light coupling system comprising at least one telecentric element and a plurality of light mixing rods, wherein each sample region is assigned at least one of the light mixing rods, wherein the telecentric element is disposed between the light source and the plurality of sample regions, wherein plurality of light mixing rods are tapered such that a narrower end of each light mixing rod faces the plurality of sample regions, and the plurality of light mixing rods is disposed between the telecentric element and the plurality of sample regions;

a detector disposed to receive light beams originating from the plurality of sample regions, wherein an optical detection system is further disposed between the plurality of sample regions and the detector, said optical detection system comprising the telecentric element and the plurality of light mixing rods, such that the light originating from the plurality of sample regions passes the telecentric element and the plurality of light mixing rods of the optical detection system.

Embodiment 2

The apparatus of embodiment 1, wherein said telecentric element is independently selected from a field lens, a refractive field lens, a merged refractive field lens, a Fresnel field lens, a prism array, a Fresnel prism array, prisms.

Embodiment 3

The apparatus of any of embodiments 1 to 2, wherein the telecentric element and the plurality of mixing rods are physically separate units Embodiment 4

The apparatus of any of embodiments 1 to 3, wherein the telecentric element and the plurality of mixing rods are in physical contact with each other.

Embodiment 5

The apparatus of any of embodiments 1 to 4, wherein the telecentric element and the plurality of light mixing rods are at least partially made of glass or plastics.

Embodiment 6

The apparatus of any of embodiments 1 to 5, wherein the telecentric element and the plurality of light mixing rods are bonded, adhered welded or mechanically connected to one another.

Embodiment 7

The apparatus of any of embodiments 1 to 6, wherein the telecentric element and the plurality of light mixing rods are integrally formed.

Embodiment 8

The apparatus of embodiment 7, wherein the telecentric element and the plurality of light mixing rods are integrally molded.

Embodiment 9

The apparatus of any of embodiments 1 to 8, wherein a cover against stray light is disposed between the plurality of light mixing rods.

Embodiment 10

The apparatus of embodiment 9, wherein the cover is a grid shaped plate.

Embodiment 11

The apparatus according to any of embodiments 1 to 10, wherein the plurality of light mixing rods comprise at least 2, preferably at least 96 light mixing rods and more preferably multiples of 96 light mixing rods.

Embodiment 12

The apparatus of any of embodiments 1 to 11, wherein the plurality of light mixing rods comprise a rectangular cross-section.

Embodiment 13

The apparatus of any of embodiments 1 to 12, wherein the plurality of light mixing rods comprise a proximal end arranged at the telecentric element and a distal end facing the plurality of sample regions, wherein the distal ends of each of the plurality of light mixing rods are arranged in a common plane.

Embodiment 14

The apparatus of embodiment 13, wherein the plurality of light mixing rods comprise sharp edges, wherein the sharp edges are located at the distal ends of the rods.

Embodiment 15

The apparatus of embodiment 13 or 14, wherein the distal ends of each of the plurality of light mixing rods are smooth, convex, concave, slanted or angled.

Embodiment 16

The apparatus of any of embodiments 13 to 15, wherein the proximal ends of each of the plurality of light mixing rods comprise a greater numerical aperture than the distal ends.

Embodiment 17

The apparatus of any one of embodiments 13 to 16, wherein the proximal ends of the plurality of light mixing rods contact each other or are spaced apart from each other.

Embodiment 18

The apparatus of any of embodiments 1 to 17, wherein the telecentric element is a first telecentric element and the plurality of light mixing rods is a first plurality of light mixing rods, wherein the apparatus further comprises a plurality of light sources, a second telecentric element and a second plurality of light sources directly connected to the second telecentric element, wherein the second telecentric element is disposed adjacent the first telecentric element such that the second plurality of light mixing rods faces the plurality of light sources.

Embodiment 19

The apparatus of any of embodiments 1 to 18, wherein the light emitted from the light source is excitation light.

Embodiment 20

The apparatus of any of embodiments 1 to 19, wherein the light originating from the sample regions is emission light.

Embodiment 21

An analytical device for measuring an analyte comprising an apparatus according to any preceding embodiment.

Embodiment 22

The analytical device of embodiment 21, wherein the analytical device is a PCR instrument for real-time detection of nucleic acids during amplification.

Embodiment 23

An analytical system, comprising an analytical device according to embodiment 21 or 22.

Embodiment 24

Use of an apparatus according to any one of embodiments 1 to 20 for photometric measurement of biological liquids.

Embodiment 25

A method of simultaneously measuring the presence or quantity of an analyte in a sample region, comprising:
 illuminating said sample region with a light beam emitted from a light source, wherein said light beam passes a light coupling system, said light coupling system comprising a telecentric element and a plurality of light mixing rods, wherein the light coupling system is disposed between the light source and the sample region such that the light beam is directed into the sample region; and
 detecting a light beam originating from the sample region following illumination of the sample region, wherein said light beam originating from said sample region is focused onto a detector by an optical detection system disposed between the sample region and the detector.

DETAILED DESCRIPTION OF THE EMBODIMENTS

FIG. 1 a perspective view of an analytical system 110 according to a first embodiment. The analytical system 110 comprises an analytical device 112 for measuring an analyte. The analytical device 112 comprises an apparatus 114 for photometric measurement of biological liquids. The analytical device 112 may be a PCR (polymerase chain reaction) instrument for real-time detection of nucleic acids during amplification as will be explained in more detail below.

The apparatus 114 comprises a plurality of spaced apart sample regions 116, a light source 118, a lens system 120, a detector 122 and an optical detection system 124. The plurality of spaced apart sample regions 116 may be arranged in wells 126 of a support 128 such as a microtiter plate. The light source 118 is adapted to emit light comprising at least one frequency. For example, the light source 118 emits light with a single frequency. In this case, the light source 118 may be a laser or an LED. Alternatively, the light source 118 emits light comprising a plurality of frequencies. In this case, preferably the light source is a white light source, most preferably the light source 118 is a gas discharge lamp, such as a Xenon lamp or a Mercury lamp or a filament lamp, such as a Tungsten lamp.

The lens system 120 comprises a light coupling system 130. The lens system 120 further comprises at least one lens 132. For example, the lens system 120 comprises a plurality of lenses 132. The light coupling system 130 is disposed between the light source 118 and the plurality of sample regions 116. The light coupling system 130 comprises at least one telecentric element 134 and a plurality of light mixing rods 136. The telecentric element 134 may be selected from a group consisting of a field lens, a refractive field lens, a merged refractive filed lens, a Fresnel field lens, a prism array, a Fresnel prism array and prisms as will be explained in more detail below. Each sample region 116 is assigned at least one of the light mixing rods 136. The telecentric element 134 is disposed between the light source 118 and the plurality of sample regions 116. Further, the plurality of light mixing rods 136 is disposed between the telecentric element 134 and the plurality of sample regions 116. The detector 122 is disposed to receive light beams originating from the plurality of sample regions 116. The optical detection system 124 is disposed between the plurality of sample regions 116 and the detector 122. The optical detection system 124 comprises the telecentric element 134 and the plurality of light mixing rods 136 such that the light originating from the plurality of sample regions 116 passes the telecentric element 134 and the plurality of light mixing rods 136 of the optical detection system 124.

The telecentric element 134 and the plurality of light mixing rods 136 may be physically separate units. The telecentric element 134 and the plurality of light mixing rods 136 may be in physical contact with each other. Alternatively, the telecentric element 134 and the plurality of light mixing rods 136 may be at least partially made of glass or plastics. The telecentric element 134 and the plurality of light mixing rods 136 may be bonded, adhered, welded or mechanically connected to one another. The telecentric element 134 and the plurality of light mixing rods 136 may be integrally formed.

Figure 2:
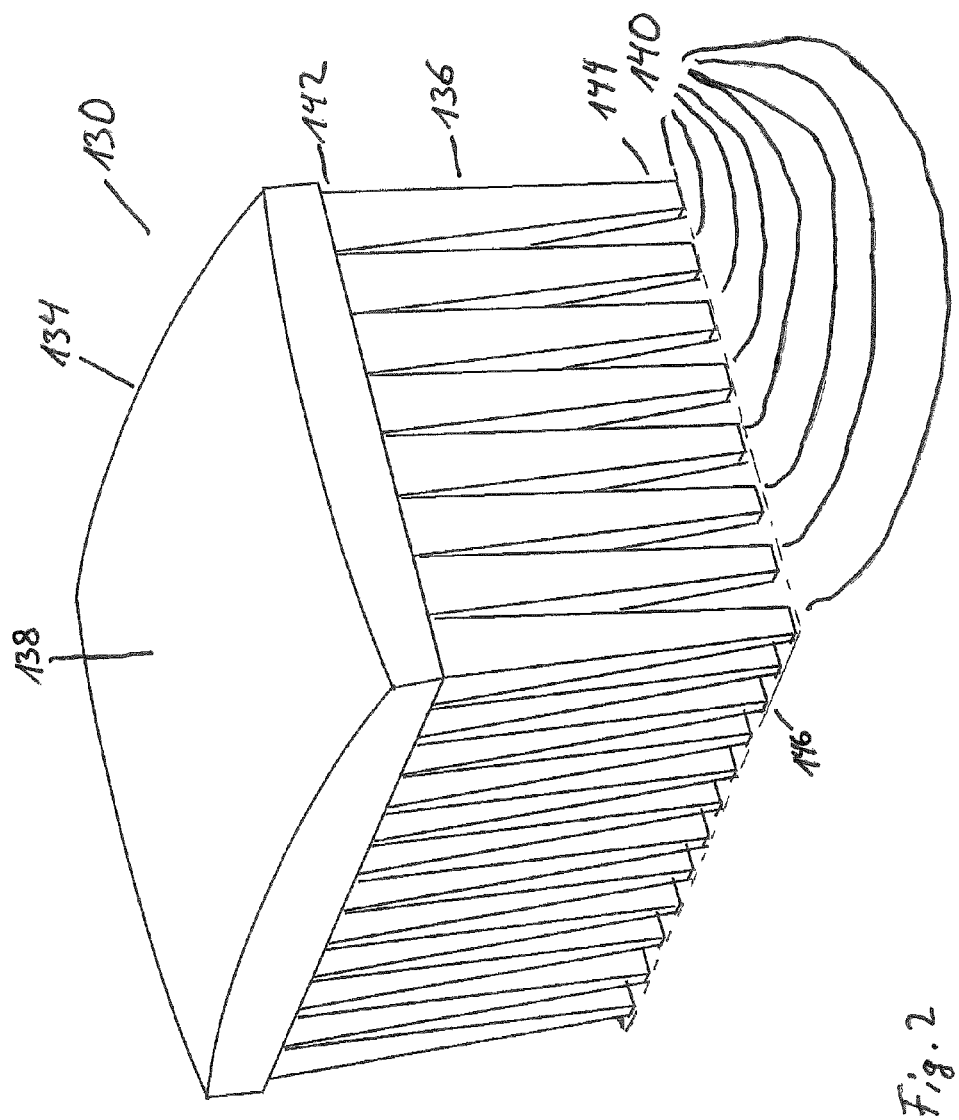
FIG. 2 shows an enlarged view of a telecentric element and a plurality of light mixing rods used with the analytical system of FIG. 1.

FIG. 2 shows an enlarged view of the telecentric element 134 and the plurality of light mixing rods 136 used with the apparatus 114 of FIG. 1. In this embodiment, the telecentric element 134 and the plurality of light mixing rods 136 are integrally molded. The telecentric element 134 of this embodiment comprises an aspheric surface 138 which is arranged on a side of the telecentric element 134 facing away from the plurality of light mixing rods 136. In a plan view of the telecentric element, which is a view from the side opposite the light mixing rods 136, the surface 138 appears to be rectangular or square. As shown in FIG. 2, the plurality of light mixing rods 136 are tapered such that a narrower end 140 of each of the light mixing rods 136 faces the plurality of sample regions 116. More particularly, each of the light mixing rods 136 comprises an upper or proximal end 142 contacting the telecentric element 134 and a lower or distal end 144 facing the plurality of sample regions 116. The distal ends 144 of each of the plurality of light mixing rods 136 are arranged in a common plane 146. The plurality of light mixing rods 136 comprises a rectangular cross-section. The light mixing rods 136 further comprises sharp edges 148 which are located at the distal end 144. Alternatively, the distal ends 144 of each of the plurality of light mixing rods 136 may be smooth, convex, concave, slanted or angled. The plurality of light mixing rods 136 may comprise at least two, preferably at least 96 light mixing rods 136 and more preferably multiples of 96 light mixing rods 136. In the embodiment shown in FIGS. 1 and 2, the plurality of light mixing rods 136 comprises 96 light mixing rods. The proximal ends 142 of each of the plurality of light mixing rods 136 comprise a greater numerical aperture than the distal ends 144. The proximal ends 142 of the plurality of light mixing rods 136 may contact each other or may be spaced apart from each other.

Figure 3:
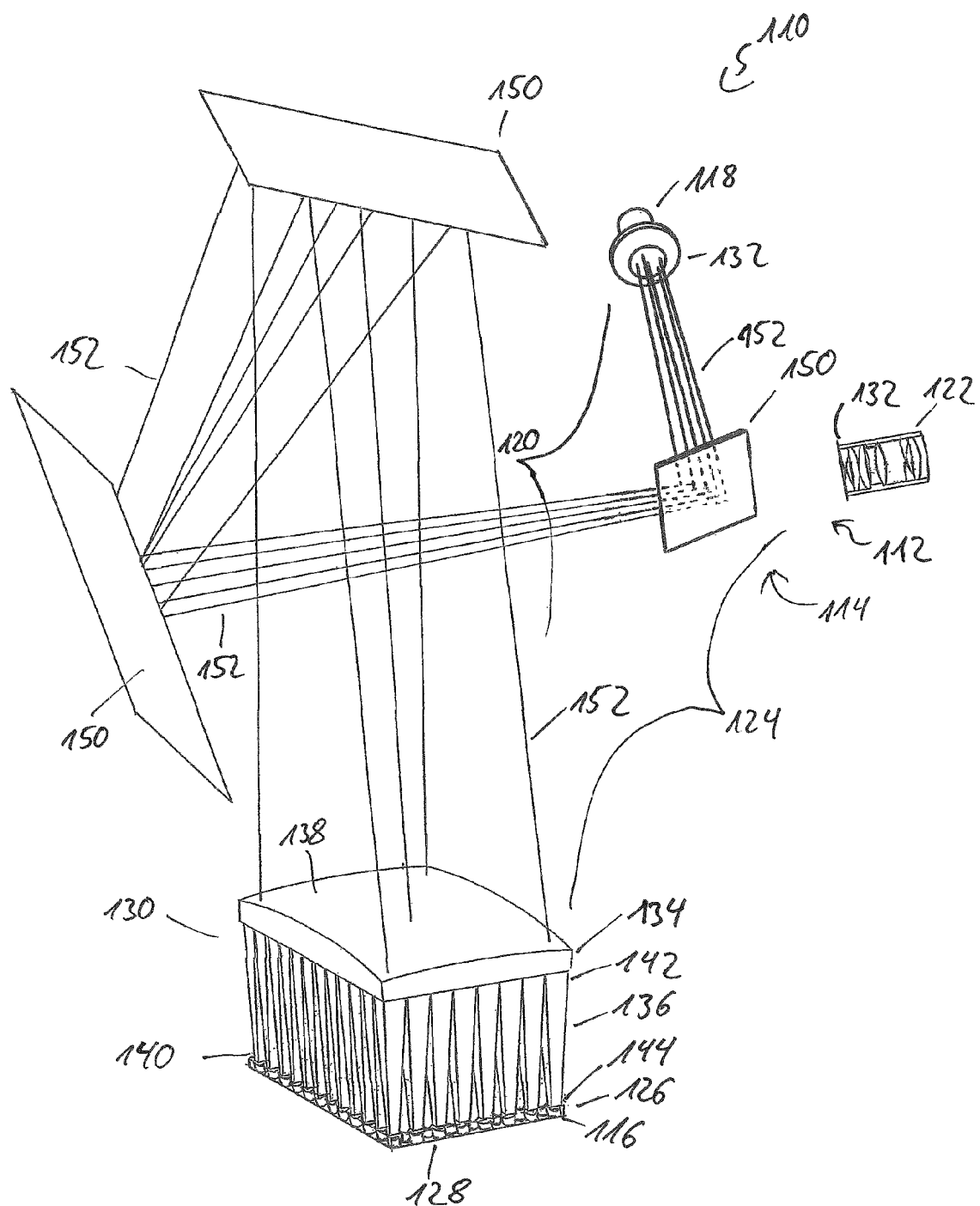
FIG. 3 shows the analytical system of FIG. 1 during illumination operation.

FIG. 3 shows the analytical system 110 of FIG. 1 during operation. More particularly, FIG. 3 shows the analytical system 110 of FIG. 1 during illumination operation. For example, the apparatus 114 may be used for photometric measurements of biological liquids. Thus, the apparatus 114 may carry out a method of simultaneously measuring the presence or quantity of an analyte in a sample region 116. The method may comprise the steps of illuminating the sample region 116 with a light beam emitted from the light source 118, wherein the light beam passes the light coupling system 134. The light beam originating from the sample region 116 is detected following illumination of the sample region 116, wherein the light beam originating from the sample region 116 is focused onto the detector 122 by the optical detection system 124.

As mentioned above, the analytical device 112 may be a PCR instrument for real-time detection of nucleic acids during amplification. Thus, the light emitted from the light source 118 is excitation light. Further, the light originating from the sample regions 116 is emission light. Further, the analytical system 110 comprises one or more mirrors or reflectors 150 for reflecting and guiding the light emitted from the light source to the sample regions 116 and the light originating from the sample regions to the detector 122.

More particularly, the apparatus 114 is an optical instrument to analyze simultaneously a plurality of PCR amplifications taking place in the wells 126 of the support 128 in the form of the microtiter plate in real time or to image the fluorescence intensity of a microarray as a measure for specific target probe interactions. In case of PCR amplifications performed in individual wells 126, all fluorescence entities are applicable as fluorescent dyes that bind specifically to double-stranded nucleic acids. In this context, these fluorescent dyes are named fluorescence DNA binding entities, whereas the fluorescence DNA binding entity is a molecule or a pair of molecules providing a characteristic fluorescence light, if they are bound to a double-stranded DNA. In the field of real-time PCR monitoring the following detection formats are known: DNA binding dye format (e.g. SybrGreenl), Taq-Man probes, Molecular Beacons, Single Labeled Probe (SLP) format or FRET hybridization probes.

In principle, there are two different strategies to excite and monitor the fluorescence of a lateral distribution of sample regions 116. The first strategy is to scan the lateral distribution of sample regions 116, whereby the individual sample regions 116 are successively analyzed one at a time. The second strategy is to illuminate the whole distribution of sample regions 116 simultaneously and to image the corresponding fluorescence e.g. on a CCD chip of the detector 122. In the present embodiment, the latter strategy is preferred.

Particularly, FIG. 3 shows the emission path of the light emitted from the light source 118. Light beams 152 emitted from the light source 118 are reflected by the mirrors 150 to the light coupling system 130 and are coupled into the telecentric element 134. Due to the aspheric surface 138 of the telecentric element 134, the light beams 152 are refracted within the telecentric element 134 such that the light beams 152 are coupled into the light mixing rods 136 such that they are parallel to one another. Thus, the light beams 152 passing the light mixing rods 136 leave the same at the distal ends 144 in a parallel manner and are guided to the sample regions 116. As each sample region 116 is assigned one of the light mixings rods 136, the light is evenly distributed to the sample regions 116. As there are 96 light mixing rods 136, the sample regions 116 are hit by 96 rays.

Light beams 152 originating from the sample regions 116 are coupled into the light mixing rods 136 at the distal ends 144 thereof. The light beams 152 pass the light mixing rods 136 and leave the same at the proximal ends 142 thereof. Then, the light beams 152 are coupled into the telecentric element 134. Due to the aspheric surface 138 of the telecentric element 134, the light beams 152 are refracted within the telecentric element 134 such that the light beams 152 are converged towards the detector 122 and all 96 rays hit a center of a lens 132 associated with the detector 122.

As can be taken from the above discussion of the operation, the telecentric element 134 is used for excitation light as well as emission light or remission light which is located within or close to a field plane. In order to prevent crosstalk between the sample regions 116, the plurality of light mixing rods 136 is provided through which the light emitted from the light source 118 as well as the light originating from the sample region 116 passes. As this plane, in which emission light beams 152 from each sample region 116 incident, is imaged in a telecentric and sharp manner onto the detector 122, crosstalk may not occur.

Figure 5:
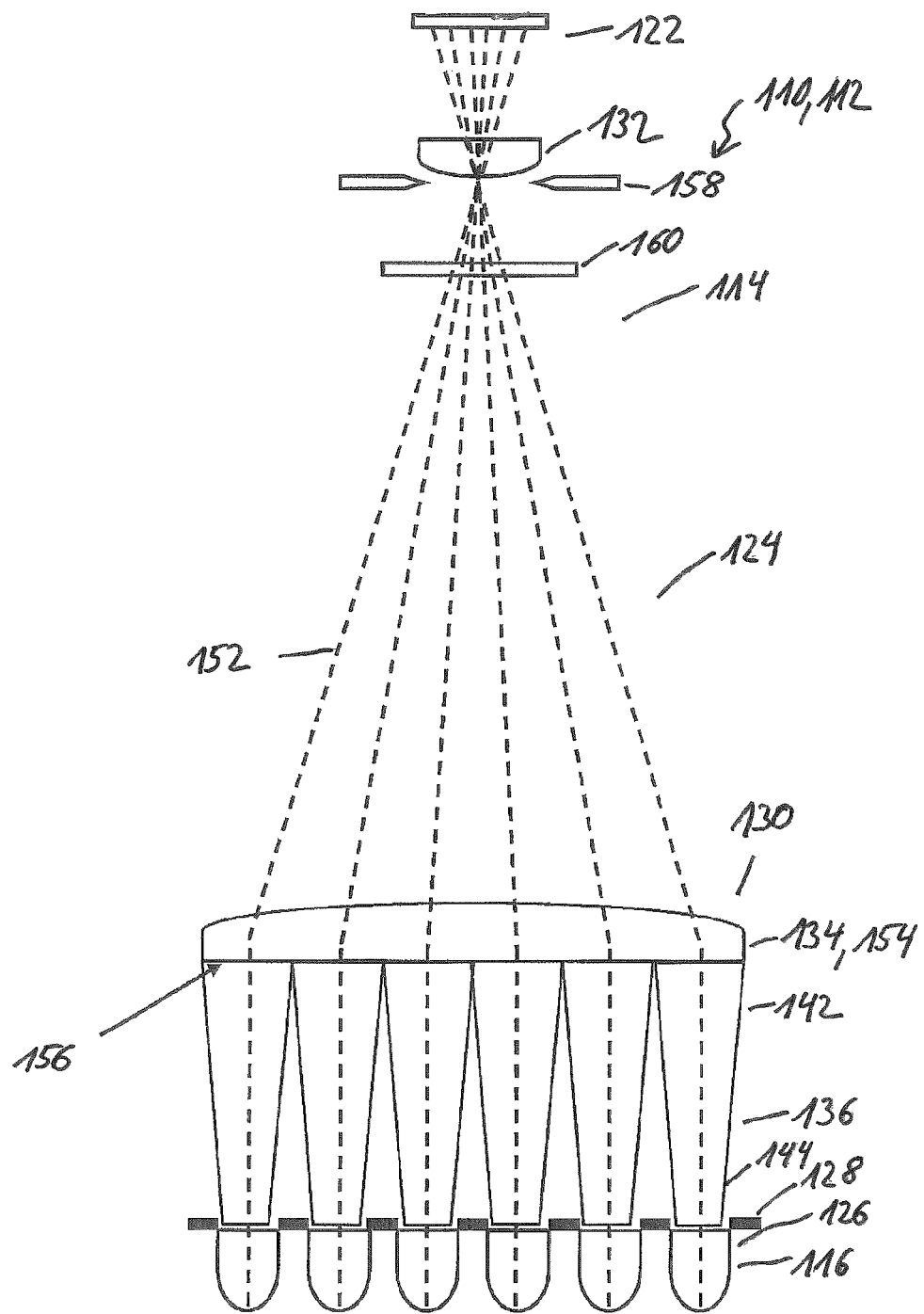
FIG. 5 shows a perspective view of an analytical system according to a second embodiment.

FIG. 5 shows a perspective view of an analytical system 110 according to a second embodiment. Hereinafter, only the differences from the first embodiment will be explained and like constructional members are indicated by identical reference signs.

Figure 4:
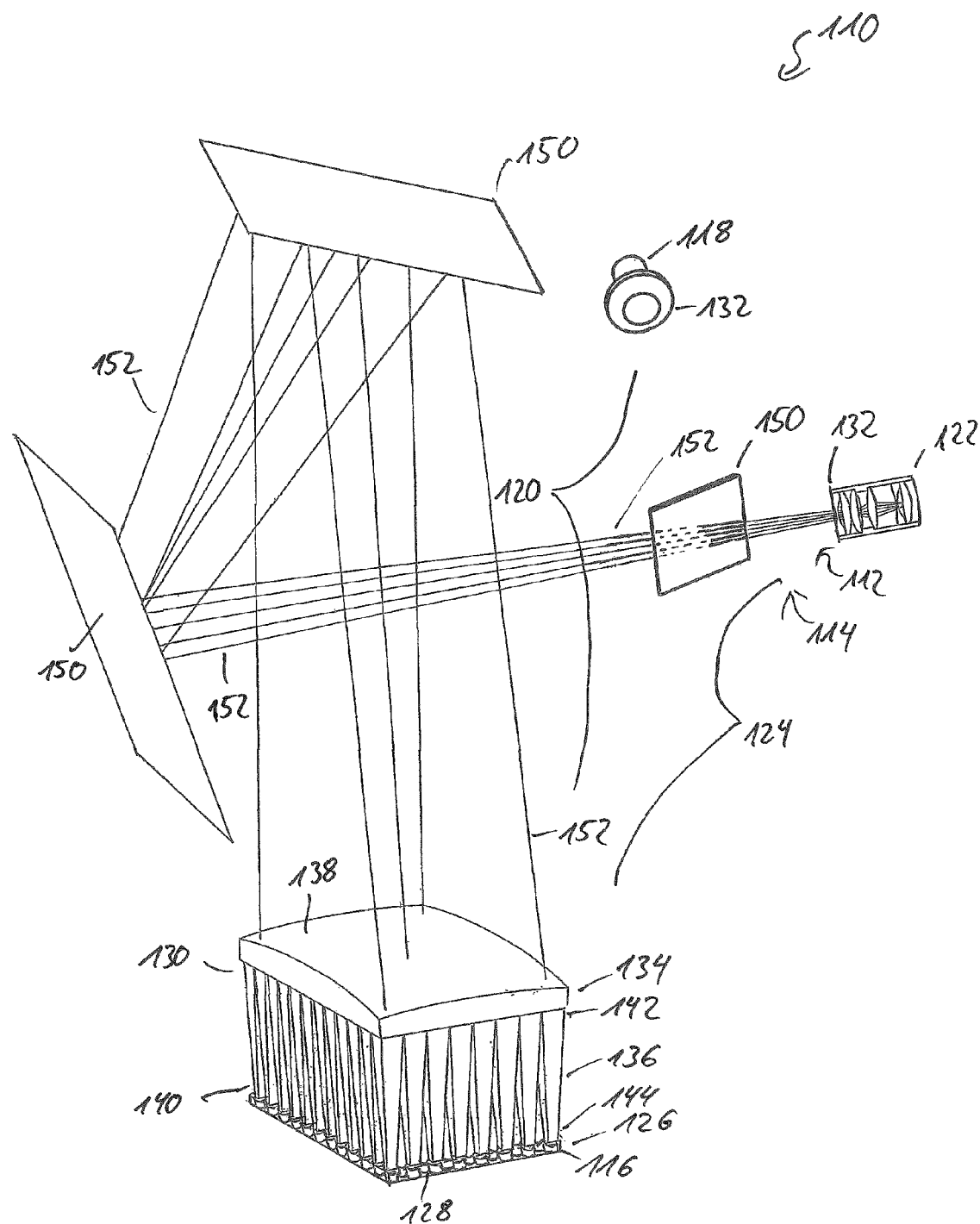
FIG. 4 shows the analytical system of FIG. 1 during detection operation.

FIG. 5 is a schematic illustration and does not show all constructional members of the analytical system 110 if compared to FIG. 1, 3 or 4. For example, the reflectors 150 are omitted only for simplification of the illustration. As shown in FIG. 5, an apparatus 114 for photometric measurement of biological liquids comprises a light coupling system 130. The light coupling system 130 comprises a telecentric element 134 which is a merged refractive field lens 154. Thus, the field lens 154 comprises an aspheric surface 138 arranged on a side opposite to a plurality of light mixing rods. The field lens 154 provides a field plane 156 which faces the plurality of light mixing rods 136. The light mixing rods 136 are attached to or integrally formed with the field lens 154 at the field plane 156. Further, there may be a lens 132, which is associated with a detector 122, a pupil stop 158 and a filter 160. As shown in FIG. 5, light beams 152 originating from a plurality of sample regions 116 are coupled into the light mixing rods 136 at the distal ends 144 thereof, pass the light mixing rods 136 parallel to one another and are refracted by the field lens 154 such that the light beams are focused within the pupil stop 158 of the lens 132 and form a sharp image on the detector 122 which is located within a further field plane (not shown). Particularly, the light beams 152 originating from a certain sample region 116 are coupled exclusively into the light mixing rod 136 assigned therewith. It is explicitly stated that the illumination operation and the detection operation may be carried out simultaneously.

Figure 6:
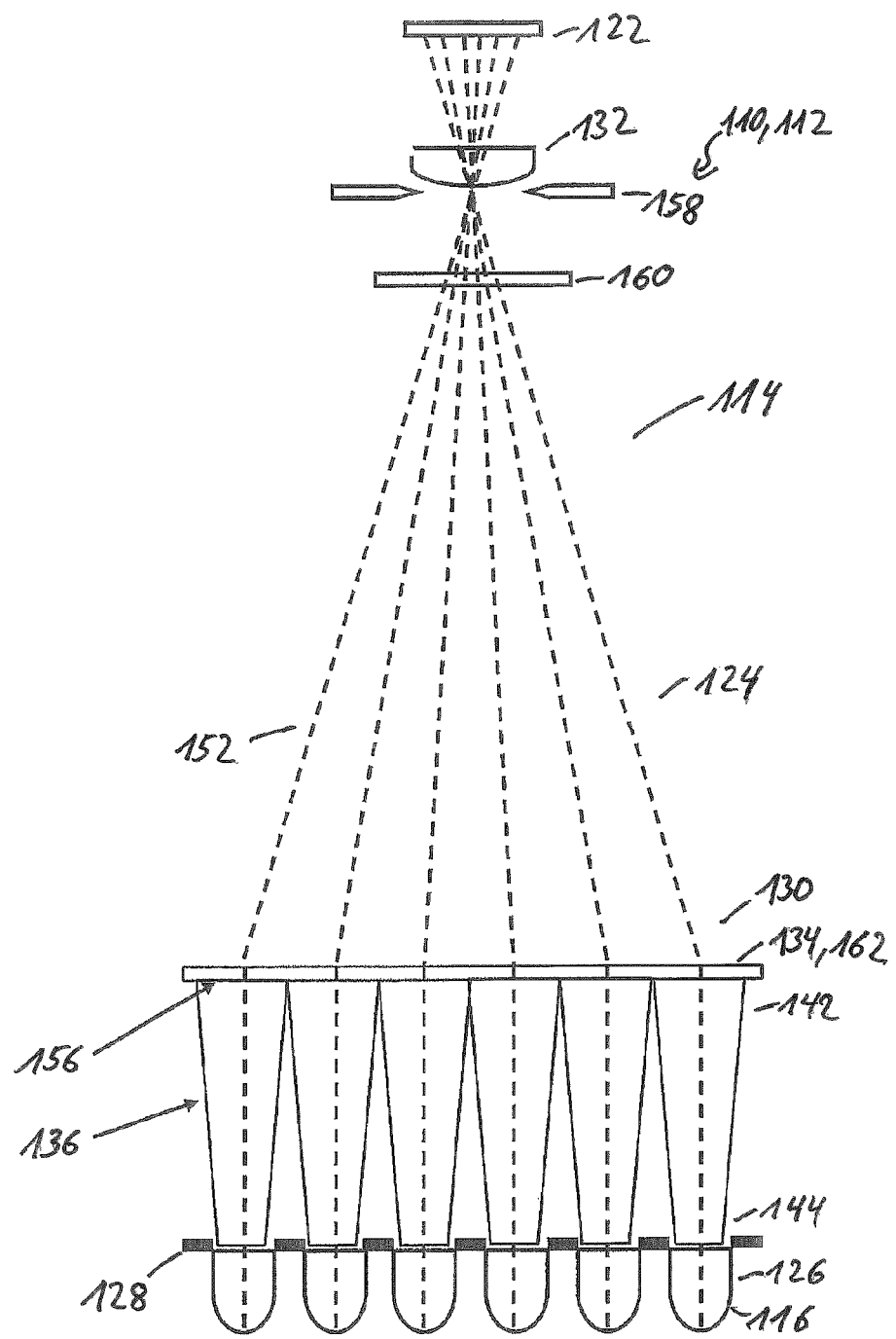
FIG. 6 shows a perspective view of an analytical system according to a third embodiment.

FIG. 6 shows a perspective view of an analytical system 110 according to a third embodiment. Hereinafter, only the differences from the previous embodiments will be explained and like constructional members are indicated by identical reference signs.

FIG. 6 is a schematic illustration and does not show all constructional members of the analytical system 110 if compared to FIG. 1, 3 or 4. For example, the reflectors 150 are omitted only for simplification of the illustration. As shown in FIG. 6, an apparatus 114 for photometric measurement of biological liquids comprises a light coupling system 130. The light coupling system 130 comprises a telecentric element 134 which is a single Fresnel field lens 162. The Fresnel field lens 162 provides a field plane 156 which faces a plurality of light mixing rods 136. The light mixing rods 136 are attached to or integrally formed with the Fresnel field lens 162 at the field plane 156. Further, there may be a lens 132 associated with a detector 122, a pupil stop 158 and a filter 160. As shown in FIG. 6, light beams 152 originating from a plurality of sample regions 116 are coupled into the light mixing rods 136 at the distal ends 144 thereof, pass the light mixing rods 136 parallel to one another and are refracted by the field lens 162 such that the light beams are focused within the pupil stop 158 of the lens 132 and form a sharp image on the detector 122 which is located within a further field plane (not shown). Particularly, the light beams 152 originating from a certain sample region 116 are coupled exclusively into the light mixing rod 136 assigned therewith. Needless to say, the above manner of transmission of light also applies to the emission side of the apparatus 114 in an opposite or vice versa manner.

Figure 7:
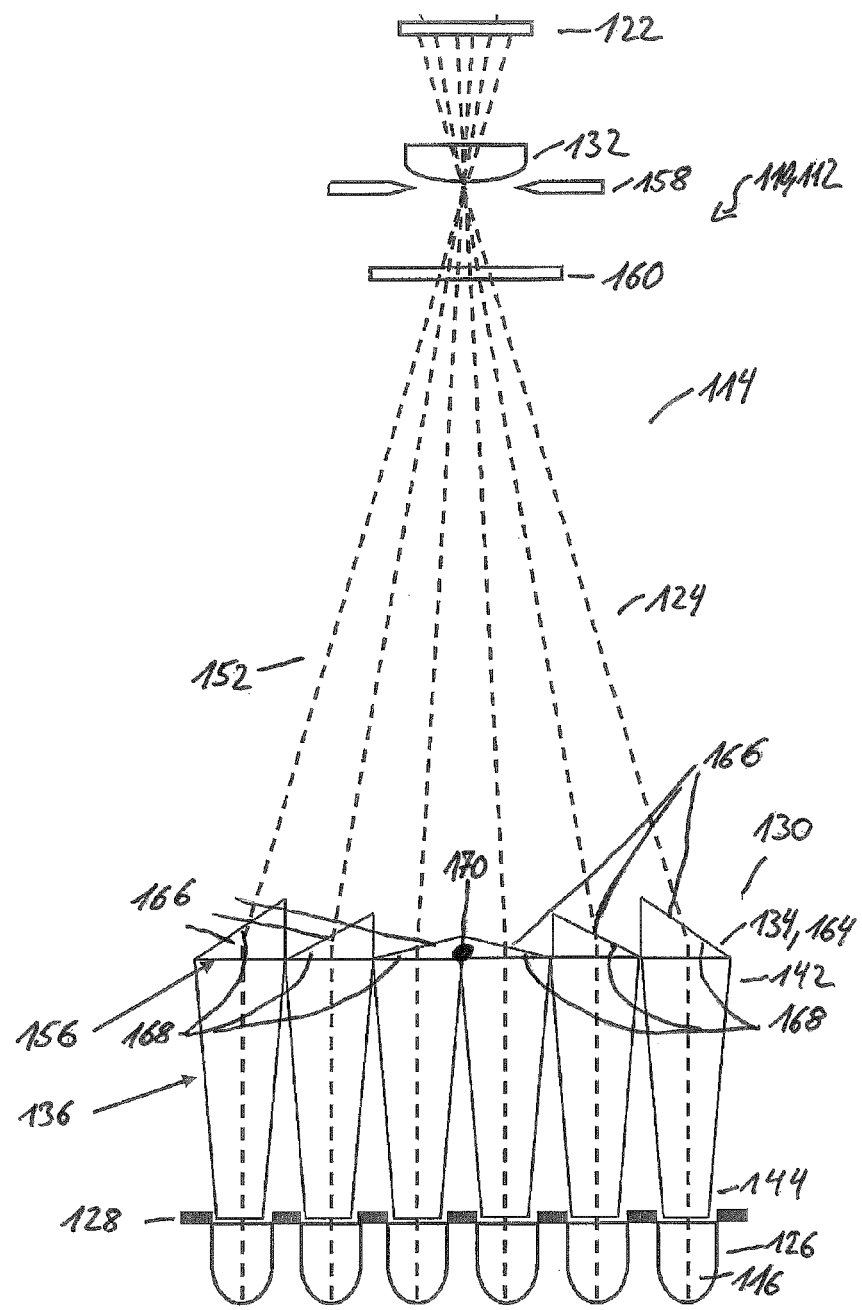
FIG. 7 shows a perspective view of an analytical system according to a fourth embodiment.

FIG. 7 shows a perspective view of an analytical system 110 according to a fourth embodiment. Hereinafter, only the differences from the previous embodiments will be explained and like constructional members are indicated by identical reference signs.

FIG. 7 is a schematic illustration and does not show all constructional members of the analytical system 110 if compared to FIG. 1, 3 or 4. For example, the reflectors 150 are omitted only for simplification of the illustration. As shown in FIG. 7, an apparatus 114 for photometric measurement of biological liquids comprises a light coupling system 130. The light coupling system 130 comprises a telecentric element 134 which is a prism array 164. The prism array 164 provides a field plane 156 which faces a plurality of light mixing rods 136. The light mixing rods 136 are attached to or integrally formed with the prism array 164 at the field plane 156. Further, there may be a lens 132 associated with a detector 122, a pupil stop 158 and a filter 160. The prism array 164 comprises a plurality of prisms 166. Each of the prisms 166 is assigned one of the light mixing rods 136. The prisms 166 may be arranged such that the prisms 166 comprise slanted surfaces 168 facing away from a middle point 170 of the prism array 164. For example, according to the illustration of FIG. 7, there are shown six prisms 166, wherein the three left prisms 166 comprise slanted surfaces 168 facing to the left with respect to the illustration of FIG. 7, whereas the three right prisms 166 comprise slanted surfaces 168 facing to the right with respect to the illustration of FIG. 7.

Further, as shown in FIG. 7, light beams 152 originating from a plurality of sample regions 116 are coupled into the light mixing rods 136 at the distal ends 144 thereof, pass the light mixing rods 136 parallel to one another and are refracted by the slanted surfaces 168 of the prisms 166 such that the light beams are focused within the pupil stop 158 of the lens 132 and form a sharp image on the detector 122 which is located within a further field plane (not shown). Particularly, the light beams 152 originating from a certain sample region 116 are coupled exclusively into the light mixing rod 136 assigned therewith.

Figure 8:
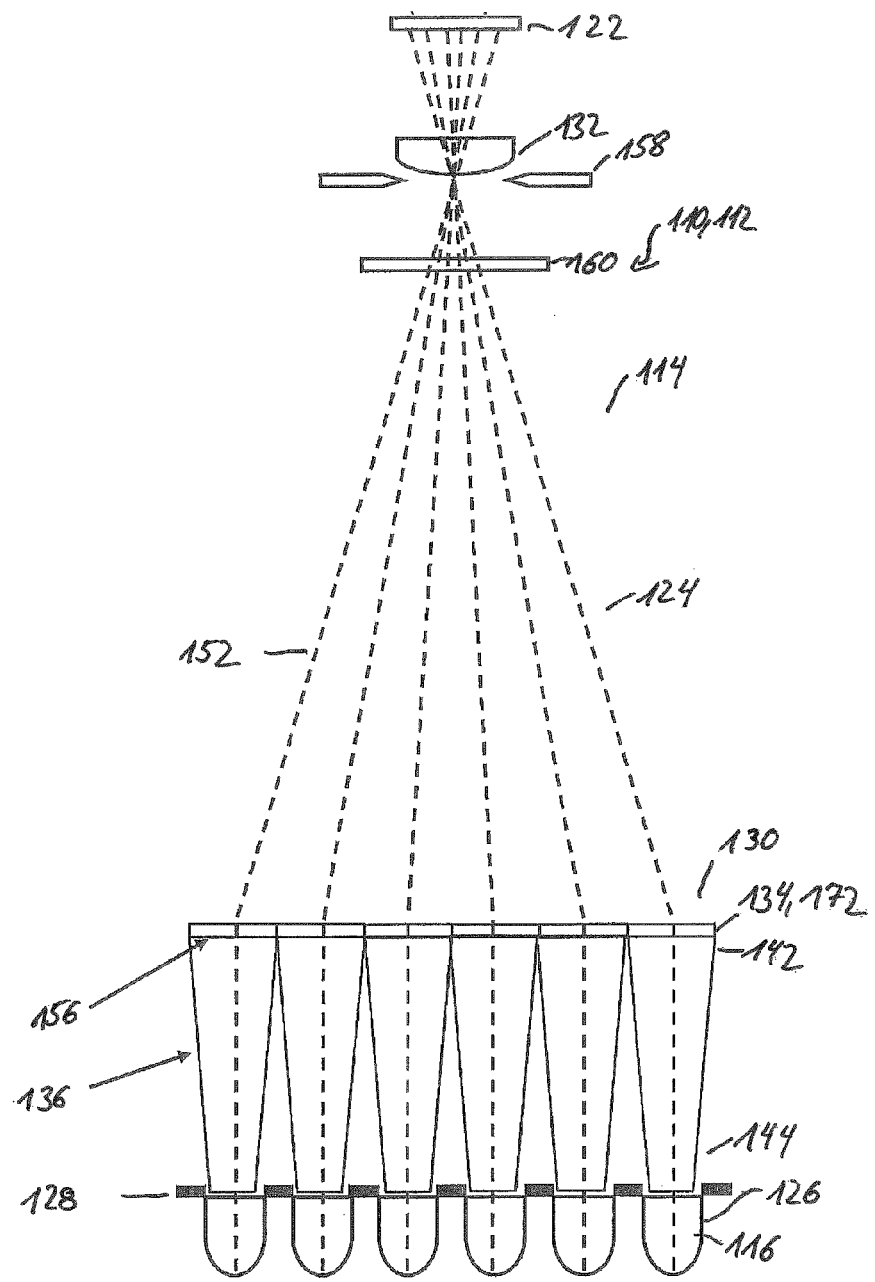
FIG. 8 shows a perspective view of analytical system according to a fifth embodiment.

FIG. 8 shows a perspective view of an analytical system 110 according to a fifth embodiment. Hereinafter, only the differences from the previous embodiments will be explained and like constructional members are indicated by identical reference signs.

FIG. 8 is a schematic illustration and does not show all constructional members of the analytical system 110 if compared to FIG. 1, 3 or 4. For example, the reflectors 150 are omitted only for simplification of the illustration. As shown in FIG. 8, an apparatus 114 for photometric measurement of biological liquids comprises a light coupling system 130. The light coupling system 130 comprises a telecentric element 134 which is a single Fresnel prism array 172. The Fresnel prism array 172 provides a field plane 156 which faces a plurality of light mixing rods 136. The light mixing rods 136 are attached to or integrally formed with the Fresnel prism array 172 at the field plane 156. Further, there may be a lens 132 associated with a detector 122, a pupil stop 158 and a filter 160. As shown in FIG. 8, light beams 152 originating from a plurality of sample regions 116 are coupled into the light mixing rods 136 at the distal ends 144 thereof, pass the light mixing rods 136 parallel to one another and are refracted by the Fresnel prism array 172 such that the light beams are focused within the pupil stop 158 of the lens 132 and form a sharp image on the detector 122 which is located within a further field plane (not shown). Particularly, the light beams 152 originating from a certain sample region 116 are coupled exclusively into the light mixing rod 136 assigned therewith.

Figure 9:
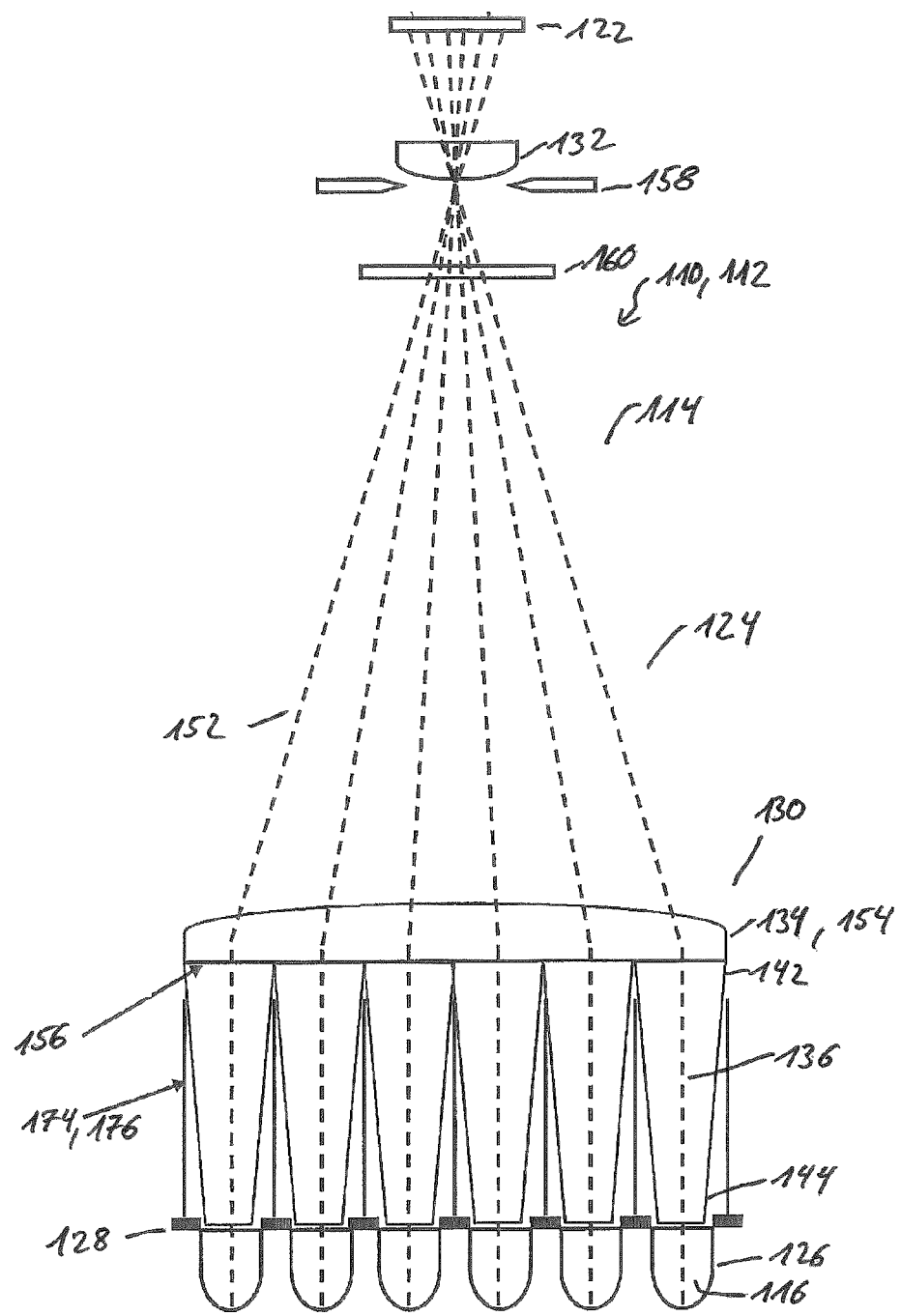
FIG. 9 shows a perspective view of an analytical system according to a sixth embodiment.

FIG. 9 shows a perspective view of an analytical system 110 according to a sixth embodiment. Hereinafter, only the differences from the previous embodiments will be explained and like constructional members are indicated by identical reference signs.

FIG. 9 is a schematic illustration and does not show all constructional members of the analytical system 110 if compared to FIG. 1, 3 or 4. For example, the reflectors 150 are omitted only for simplification of the illustration. The sixth embodiment is substantially identical with the second embodiment. Thus, an apparatus 114 for photometric measurement of biological liquids comprises a light coupling system 130. The light coupling system 130 comprises a telecentric element 134 which is a merged refractive field lens 154. Thus, the field lens 154 comprises an aspheric surface 138 arranged on a side opposite to a plurality of light mixing rods. The field lens 154 provides a field plane 156 which faces the plurality of light mixing rods 136. The light mixing rods 136 are attached to or integrally formed with the field lens 154 at the field plane 156. Further, there may be a lens 132, which is associated with a detector 122, a pupil stop 158 and a filter 160. According to the sixth embodiment, a cover 174 against stray light is disposed between the plurality of light mixing rods 136. The cover 174 may be a comb array 176.

As shown in FIG. 9, light beams 152 originating from a plurality of sample regions 116 are coupled into the light mixing rods 136 at the distal ends 144 thereof, pass the light mixing rods 136 parallel to one another and are refracted by the field lens 154 such that the light beams are focused within the pupil stop 158 of the lens 132 and form a sharp image on the detector 122 which is located within a further field plane (not shown). Particularly, the light beams 152 originating from a certain sample region 116 are coupled exclusively into the light mixing rod 136 assigned therewith. The cover 174 provides a prevention of unlikely crosstalk through air between the respective light mixing rods 136 as the respective light beams 152 are shielded from one another.

FIG. 10 shows a perspective view of a cover 174 against stray light adapted to be used with an apparatus 114 for photometric measurement of biological liquids according to any of the above embodiments. The cover according to FIG. 10 may be seen as an alternative to the cover 174 of FIG. 9. As shown in FIG. 10, the cover 174 may be a grid-shaped plate 178 which comprises evenly distributed square or rectangular openings 180. The grid-shaped plate 178 may be attached to the light coupling system 130 such that the light mixing rods 136 extend through the openings 180.

It is explicitly stated that according to any of the above embodiments, the telecentric element 134 may be a first telecentric element and the plurality of light mixing rods 136 may be a first plurality of light mixing rods. The apparatus 114 may further comprise a plurality of light sources 118, a second telecentric element and a second plurality of light sources (not shown) directly connected to the second telecentric element. The second telecentric element may be disposed adjacent to the first telecentric element such that the second plurality of light mixing rods faces the plurality of light sources. Thus, the first and second telecentric elements as well as the first and second pluralities of light mixings rods are arranged in a mirror symmetrical manner. This arrangement may further prevent any crosstalk.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

LIST OF REFERENCE NUMBERS 110 analytical system
112 analytical device
114 apparatus for photometric measurement of biological liquids
116 sample region
118 light source
120 lens system
122 detector
124 optical detection system
126 wells
128 support
130 light coupling system
132 lens
134 telecentric element
136 light mixing rod
138 surface
140 narrower end
142 proximal end
144 distal end
146 plane
148 edge
150 reflector
152 light beam
154 field lens
156 field plane
158 pupil stop
160 filter
162 Fresnel field lens
164 prism array
166 prism
168 slanted surface
170 middle point
172 Fresnel prism array
174 cover
176 comb array
178 grid-shaped plate
180 opening While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An apparatus (114) for photometric measurement of biological liquids comprising:
    a plurality of spaced apart sample regions (116);
    a light source (118) adapted to emit light comprising at least one frequency;
    a lens system (120) comprising a light coupling system (130), wherein the light coupling system (130) is disposed between the light source (118) and the plurality of sample regions (116), the light coupling system (130) comprising at least one telecentric element (134) and a plurality of light mixing rods (136), wherein each sample region (116) is assigned at least one of the light mixing rods (136), wherein the telecentric element (134) is disposed between the light source (118) and the plurality of sample regions (116), wherein the plurality of light mixing rods (136) is tapered such that a narrower end (140) of each light mixing rod (136) faces the plurality of sample regions (116), and the plurality of light mixing rods (136) is disposed between the telecentric element (134) and the plurality of sample regions (116);
    a detector (122) disposed to receive light beams (152) originating from the plurality of sample regions (116),
    wherein an optical detection system (124) is further disposed between the plurality of sample regions (116) and the detector (122), said optical detection system (124) comprising the telecentric element (134) and the plurality of light mixing rods (136), such that the light originating from the plurality of sample regions (116) passes the telecentric element (134) and the plurality of light mixing rods (136) of the optical detection system (124).

2. The apparatus (114) of claim 1, wherein said telecentric element (134) is independently selected from a field lens, a refractive field lens, a merged refractive field lens (154), a Fresnel field lens (162), a prism array (164), a Fresnel prism array (172), prisms (166).

3. The apparatus (114) of claim 1, wherein the telecentric element (134) and the plurality of light mixing rods (136) are integrally formed.

4. The apparatus (114) of claim 1, wherein a cover (174) against stray light is disposed between the plurality of light mixing rods (136).

5. The apparatus (114) of claim 1, wherein the plurality of light mixing rods (136) comprises a rectangular cross-section.

6. The apparatus (114) of claim 1, wherein the plurality of light mixing rods (136) comprise at least 2, preferably at least 96 light mixing rods (136) and more preferably multiples of 96 light mixing rods (136).

7. The apparatus (114) of claim 1, wherein the plurality of light mixing rods (136) comprise a proximal end (142) arranged at the telecentric element (134) and a distal end (144) facing the plurality of sample regions (116), wherein the distal ends (144) of each of the plurality of light mixing rods (136) are arranged in a common plane (146).

8. The apparatus (114) of claim 7, wherein the plurality of light mixing rods (136) comprise sharp edges (148), wherein the sharp edges (148) are located at the distal ends (144) of the rods (136).

9. The apparatus (114) of claim 7, wherein the distal ends (144) of each of the plurality of light mixing rods (136) comprise a greater numerical aperture than the proximal ends (142).

10. An analytical device (112) for measuring an analyte comprising an apparatus (114) according to claim 1.

11. The analytical device (112) of claim 10, wherein the analytical device (112) is a PCR instrument for real-time detection of nucleic acids during amplification.

12. An analytical system (110), comprising an analytical device (112) according to claim 10.

\* \* \* \* \*